US 11,898,751 B2
(12) United States Patent
Kawabe et al.

(10) Patent No.: US 11,898,751 B2
(45) Date of Patent: Feb. 13, 2024

(54) METHOD AND DEVICE FOR PREDICTING ASH ADHESION IN COAL-FIRED BOILER, METHOD AND DEVICE FOR PREVENTING ASH ADHESION IN COAL-FIRED BOILER, AND METHOD AND DEVICE FOR OPERATING COAL-FIRED BOILER

(71) Applicants: IHI Corporation, Tokyo (JP); IHI INSPECTION AND INSTRUMENTATION CO., LTD., Tokyo (JP)

(72) Inventors: Hirotaka Kawabe, Tokyo (JP); Kenjiro Chie, Tokyo (JP); Junichi Shigeta, Tokyo (JP)

(73) Assignees: IHI Corporation, Tokyo (JP); IHI INSPECTION AND INSTRUMENTATION CO., LTD., Tokyo (JP)

( * ) Notice: Subject to any disclaimer, the term of this patent is extended or adjusted under 35 U.S.C. 154(b) by 407 days.

(21) Appl. No.: 17/168,247
(22) Filed: Feb. 5, 2021
(65) Prior Publication Data US 2021/0156561 A1 May 27, 2021

Related U.S. Application Data

(63) Continuation of application No. PCT/JP2019/032868, filed on Aug. 22, 2019.

(30) Foreign Application Priority Data

Sep. 3, 2018 (JP) .................................. 2018-164614

(51) Int. Cl.
*F23N 1/00* (2006.01)
*F23N 5/00* (2006.01)
(52) U.S. Cl.
CPC ............. *F23N 5/003* (2013.01); *F23N 1/002* (2013.01); *F23N 2221/10* (2020.01);
(Continued)

(58) Field of Classification Search
USPC .......................................................... 431/76
See application file for complete search history.

(56) References Cited

U.S. PATENT DOCUMENTS 3,475,599 A * 10/1969 Schwartzenberg ...... G06G 7/58
73/23.31
7,553,463 B2 * 6/2009 Zauderer .................... F23J 9/00
110/255
(Continued)

FOREIGN PATENT DOCUMENTS

JP 2004-361368 A 12/2004
JP 2009218314 A * 9/2009 ........... H05K 9/0081
(Continued)

OTHER PUBLICATIONS

International Search Report dated Oct. 21, 2019 in PCT/JP2019/032868 filed on Aug. 22, 2019, 2 pages.
(Continued)

*Primary Examiner* — Avinash A Savani
(74) *Attorney, Agent, or Firm* — Oblon, McClelland, Maier & Neustadt, L.L.P.

(57) ABSTRACT

Conducted are coal-ash generating step for generating coal ash, sintered-ash generating step for heating the coal ash at temperatures within combustion temperature range of coal-fired boiler to generate sintered ash at each heating temperature, sticking-degree calculating step for rotatively separating each sintered ash by ratra tester to calculate sticking degree from weight ratio of each sintered ash after and before the rotary separation of the sintered ash, correlation determining step for burning each coal having corresponding sticking degree calculated to measure exhaust gas temperature and obtain correlation between sticking degrees and exhaust gas temperatures, exhaust-gas-temperature predicting step for predicting exhaust gas temperature from sticking degree of coal to be employed as fuel based on the correlation between the sticking degrees and the exhaust gas temperatures and adhesion predicting step for predicting ash
(Continued)

adhesion in the coal-fired boiler based on the exhaust gas temperature predicted.

12 Claims, 8 Drawing Sheets

(52) U.S. Cl.
CPC ...... *F23N 2225/10* (2020.01); *F23N 2239/02* (2020.01); *F23N 2241/10* (2020.01)

(56) References Cited

U.S. PATENT DOCUMENTS

| | | | |
|---|---|---|---|
| 2012/0023823 A1* | 2/2012 | D'Agostini | F23G 5/12 |
| | | | 48/197 R |
| 2012/0174836 A1* | 7/2012 | Akiyama | F22B 37/107 |
| | | | 110/186 |
| 2018/0320097 A1* | 11/2018 | Sakai | C10L 9/10 |

FOREIGN PATENT DOCUMENTS

| | | | |
|---|---|---|---|
| JP | 2011-080727 A | | 4/2011 |
| JP | 2012-013252 A | | 1/2012 |
| JP | 2012-013253 A | | 1/2012 |
| JP | 2012013253 A | * | 1/2012 |
| JP | 2016-205681 A | | 12/2016 |

OTHER PUBLICATIONS

Couch, "Understanding slagging and fouling in pf combustion", IEACR-72, 1994, 3 pages (Abstract only).

\* cited by examiner

METHOD AND DEVICE FOR PREDICTING ASH ADHESION IN COAL-FIRED BOILER, METHOD AND DEVICE FOR PREVENTING ASH ADHESION IN COAL-FIRED BOILER, AND METHOD AND DEVICE FOR OPERATING COAL-FIRED BOILER

TECHNICAL FIELD

The present disclosure relates to a method and a device for predicting ash adhesion in a coal-fired boiler, a method and a device for preventing ash adhesion in a coal-fired boiler and a method and a device for operating a coal-fired boiler.

BACKGROUND ART

Generally in a coal-fired boiler, pulverized coal is burned to generate ash melted in combustion gas, which may result in a trouble such as so-called slagging or fouling where the ash adheres to and becomes deposited on furnace walls or heat transmission tubes in a boiler body. Such ash adhesion and deposition may cause significant lowering of heat recovery on the heat transmission surfaces such as the furnace walls or heat transmission tubes. Moreover, lamination of huge clinker on the furnace walls may cause troubles such as drastic pressure fluctuation in the furnace and clogging of a furnace bottom due to droppage of the clinker.

Furthermore, especially an upper heat transfer unit provided at an upper portion of the furnace and comprising secondary, tertiary and final superheaters and a secondary repeater is constructed to conduct heat exchange by combustion gas flowing through the heat transmission tubes arranged at narrow intervals. Thus, ash adhesion on the upper heat transfer unit may cause drastic pressure fluctuation in the furnace and clogging of gas flow passages, inevitably resulting in shutdown of the coal-fired boiler.

Thus, for a stable operation of the coal-fired boiler, it is necessary to predict in advance a possibility of ash adhesion during combustion of coal fuel in the boiler.

To this end, conventionally, attempts have been made to express the possibility of ash adhesion as an index; used in general are indices and evaluation criteria on ash on the basis of ash composition representing ash-containing elements in the form of oxides (see, for example, Non-patent Literature 1).

The indices and evaluation criteria on ash shown in Non-patent Literature 1 are defined for bituminous coal which is high-grade coal less problematic on, for example, ash adhesion.

It has been pointed out that the indices shown in Non-patent Literature 1 are not highly reliable since a relationship between the indices and ash adhesion shown in Non-patent Literature 1 does not always have a consistent tendency; there is a problem that the conventional indices cannot be used for some kinds of coal regarded as low-grade coal such as subbituminous coal, high-silica coal, high-sulfur coal, high-calcium coal and high-ash coal. In some cases, ash damages have occurred due to use of coal regarded as non-problematic one by the conventional indices.

On the other hand, it has been recently demanded to use low-grade coal, for example, from an economic viewpoint and from the fact that stable procurement of high-grade coal becomes difficult due to reduction in output of the high-grade coal. Thus, new indices have been required which can cope with ash resulting from combustion of such low-grade coal.

Bearing in mind such demand, it has been disclosed to evaluate an ash adhesion property on the basis of a slag viscosity at a predetermined atmospheric temperature in a mixture of various kinds of solid fuel including low-grade coal (see, for example, Patent Literature 1).

CITATION LIST

Patent Literature

Patent Literature 1: JP 2011-080727A

Non-Patent Literature

Non-patent Literature 1: Understanding slagging and fouling in pf combustion (IEACR/72), 1994

SUMMARY

Technical Problems

However, with regard to low-grade coal such as subbituminous coal on which little knowledge has been accumulated, it is difficult to precisely grasp slag adhesion behaviors in an actual boiler from a numerically valued slag viscosity calculated on the basis of chemical composition and the like as disclosed in Patent Literature 1. Moreover, in reality, it is considered difficult to determine and calculate a slag viscosity in heating of coal or other solid fuel at an ambient temperature as high as, for example, 1300° C.

In view of the above conventional problems, the present disclosure discloses a method and a device for predicting ash adhesion in a coal-fired boiler, a method and a device for preventing ash adhesion in a coal-fired boiler and a method and a device for operating a coal-fired boiler, which can grasp a correlation between sticking degrees and exhaust gas temperatures to suppress lowering of operation availability due to ash damages and effectively utilize economically advantageous low-grade coal.

Solution to Problems

The disclosure is directed to a method for predicting ash adhesion in a coal-fired boiler comprising
  a coal-ash generating step for asking coal into coal ash,
  a sintered-ash generating step for heating the coal ash generated in said coal-ash generating step at a plurality of temperatures within a combustion temperature range of the coal-fired boiler to generate sintered ash at each of the heating temperatures,
  a sticking-degree calculating step for rotatively separating each sintered ash generated in said sintered-ash generating step by a ratra tester to calculate a sticking degree from a weight ratio of each sintered ash after and before the rotary separation thereof,
  a correlation determining step for burning each coal having a corresponding sticking degree calculated in said sticking-degree calculating step in the coal-fired boiler to measure an exhaust gas temperature to thereby determine a correlation between sticking degrees and exhaust gas temperatures,
  an exhaust-gas-temperature predicting step for predicting an exhaust gas temperature from a sticking degree of coal to be employed as fuel on the basis of the correlation between the sticking degrees and the exhaust gas temperatures obtained in said correlation determining step and an adhesion predicting step for predicting ash adhesion in the coal-fired boiler on the basis of the exhaust gas temperature predicted in said exhaust-gas-temperature predicting step.

In the method for predicting ash adhesion in the coal-fired boiler, said coal may be a mixture of a plurality kinds of coal.

The disclosure is also directed to a device for predicting ash adhesion in a coal-fired boiler comprising a coal-ash generator for ashing coal into coal ash, a sintered-ash generator for heating the coal ash generated in said coal-ash generator at a plurality of temperatures within a combustion temperature range of the coal-fired boiler to generate sintered ash at each of the heating temperatures, a ratra tester for rotatively separating each sintered ash generated in said sintered-ash generator, a sticking-degree calculator for calculating a sticking degree from a weight ratio of each sintered ash after and before the rotary separation thereof by said ratra tester, a correlation determiner for burning each coal having a corresponding sticking degree calculated in said sticking-degree calculator in the coal-fired boiler to measure an exhaust gas temperature to thereby determine a correlation between sticking degrees and exhaust gas temperatures, an exhaust-gas-temperature predictor for predicting an exhaust gas temperature from a sticking degree of coal to be employed as fuel on the basis of the correlation between the sticking degrees and the exhaust gas temperatures obtained in said correlation determiner and an adhesion predictor for predicting ash adhesion in the coal-fired boiler on the basis of the exhaust gas temperature predicted in said exhaust-gas-temperature predictor.

In the device for predicting ash adhesion in the coal-fired boiler, said coal may be a mixture of a plurality of kinds of coal.

The disclosure is also directed to a method for preventing ash adhesion in a coal-fired boiler comprising a coal-ash generating step for asking coal into coal ash, a sintered-ash generating step for heating the coal ash generated in said coal-ash generating step at a plurality of temperatures within a combustion temperature range of the coal-fired boiler to generate sintered ash at each of the heating temperatures, a sticking-degree calculating step for rotatively separating each sintered ash generated in said sintered-ash generating step by a ratra tester to calculate a sticking degree from a weight ratio of the sintered ash after and before the rotary separation thereof, a correlation determining step for burning each coal having a corresponding sticking degrees calculated in said sticking-degree calculating step in the coal-fired boiler to measure an exhaust gas temperature to thereby determine a correlation between sticking degrees and exhaust gas temperatures and a coal selecting step for selecting coal having a sticking degree as fuel so as to provide an exhaust gas temperature not higher than a set value on the basis of the correlation between the sticking degrees and the exhaust gas temperatures obtained in said correlation determining step.

In the method for preventing ash adhesion in the coal-fired boiler, said coal may be a mixture of a plurality of kinds of coal.

The disclosure is also directed to an device for preventing ash adhesion in a coal-fired boiler comprising a coal-ash generator for asking coal into coal ash, a sintered-ash generator for heating the coal ash generated in said coal-ash generator at a plurality of temperatures within a combustion temperature range of the coal-fired boiler to generate sintered ash at each of the heating temperatures, a ratra tester for rotatively separating each sintered ash generated in said sintered-ash generator, a sticking-degree calculator for calculating a sticking degree from a weight ratio of each sintered ash after and before the rotary separation thereof by said ratra tester, a correlation determiner for burning each coal having a corresponding sticking degree calculated in said sticking-degree calculator in the coal-fired boiler to measure an exhaust gas temperature to thereby determine a correlation between sticking degrees and exhaust gas temperatures and a coal selector for selecting coal with a sticking degree as fuel so as to provide an exhaust gas temperature not higher than a set value on the basis of the correlation between the sticking degrees and the exhaust gas temperatures obtained in said correlation determiner.

In the device for preventing ash adhesion in the coal-fired boiler, said coal may be a mixture of a plurality of kinds of coal.

The disclosure is also directed to a method for operating a coal-fired boiler comprising a coal-ash generating step for asking coal into coal ash, a sintered-ash generating step for heating the coal ash generated in said coal-ash generating step at a plurality of temperatures within a combustion temperature range of the coal-fired boiler to generate sintered ash at each of the heating temperatures, a sticking-degree calculating step for rotatively separating each sintered ash generated in said sintered-ash generating step by a ratra tester to calculate a sticking degree from a weight ratio of the sintered ash after and before the rotary separation thereof, a correlation determining step for burning each coal having a corresponding sticking degree calculated in said sticking-degree calculating step in the coal-fired boiler to measure an exhaust gas temperature to thereby determine a correlation between sticking degrees and exhaust gas temperatures, an exhaust-gas-temperature predicting step for predicting an exhaust gas temperature from a sticking degree of coal to be employed as fuel on the basis of the correlation between the sticking degrees and the exhaust gas temperatures obtained in said correlation determining step and a combustion-time adjusting step for adjusting a combustion time of said coal on the basis of the exhaust gas temperature predicted in said exhaust-gas-temperature predicting step.

In the method for operating the coal-fired boiler, said coal may be a mixture of a plurality of kinds of coal.

The disclosure is also directed to a device for operating a coal-fired boiler comprising a coal-ash generator for ashing coal into coal ash, a sintered-ash generator for heating the coal ash generated in said coal-ash generator at a plurality of temperatures within a combustion temperature range of the coal-fired boiler to generate sintered ash at each of the heating temperatures, a ratra tester for rotatively separating each sintered ash generated in said sintered-ash generator, a sticking-degree calculator for calculating a sticking degree from a weight ratio of each sintered ash after and before the rotary separation thereof by said ratra tester, a correlation determiner for burning each coal having a corresponding sticking degree calculated in said sticking-degree calculator in the coal-fired boiler to measure an exhaust gas temperature to thereby determine a correlation between sticking degrees and exhaust gas temperatures, an exhaust-gas-temperature predictor for predicting an exhaust gas temperature from a sticking degree of coal to be employed as fuel on the basis of the correlation between the sticking degrees and the exhaust gas temperatures obtained in said correlation determiner and a combustion-time adjuster for adjusting a combustion time of said coal on the basis of the exhaust gas temperature predicted in said exhaust-gas-temperature predictor.

In the device for operating the coal-fired boiler, said coal may be a mixture of a plurality of kinds of coal.

Effect

A method and a device for predicting ash adhesion in a coal-fired boiler, a method and a device for preventing ash adhesion in a coal-fired boiler and a method and a device for operating a coal-fired boiler according to the disclosure can exhibit an excellent effect that a correlation between sticking degrees and exhaust gas temperatures can be grasped to suppress lowering of operation availability due to ash damages and effectively utilize economically advantageous low-grade coal.

DESCRIPTION OF EMBODIMENTS

Embodiments of the disclosure will be described in conjunction with attached drawings.

Figure 1:
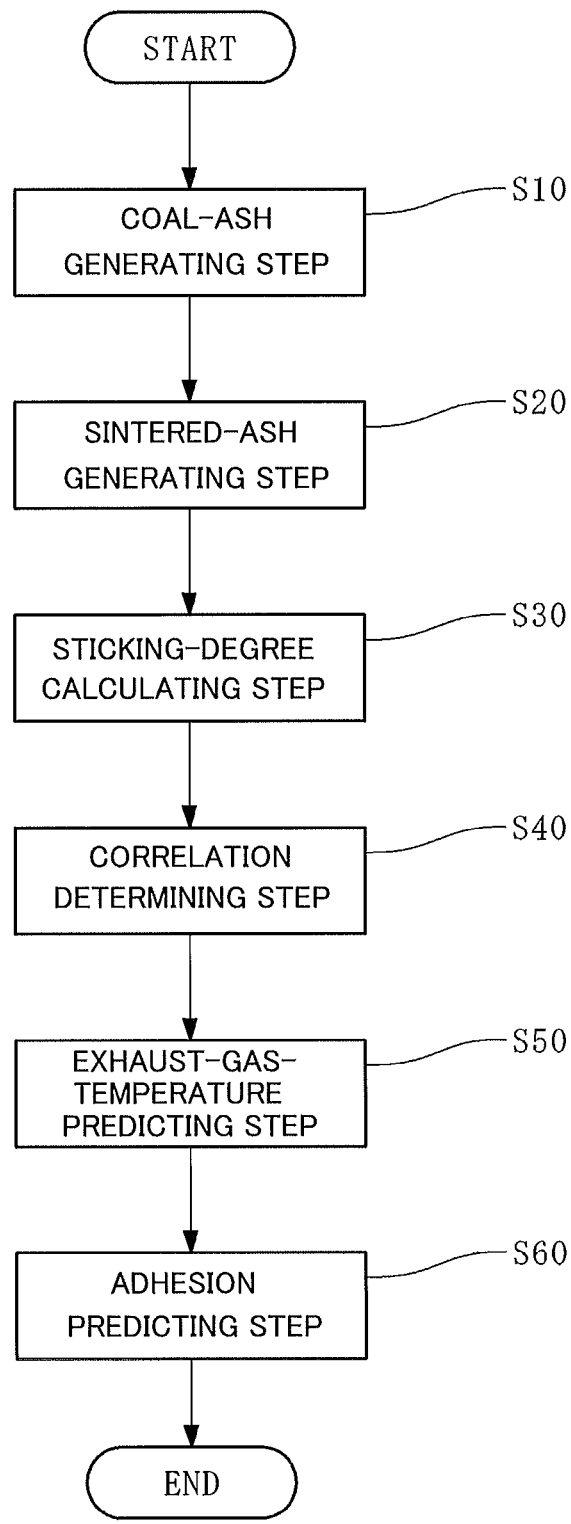
FIG. 1 is a flowchart for showing an embodiment of a method for predicting ash adhesion in a coal-fired boiler according to the disclosure.
Figure 2:
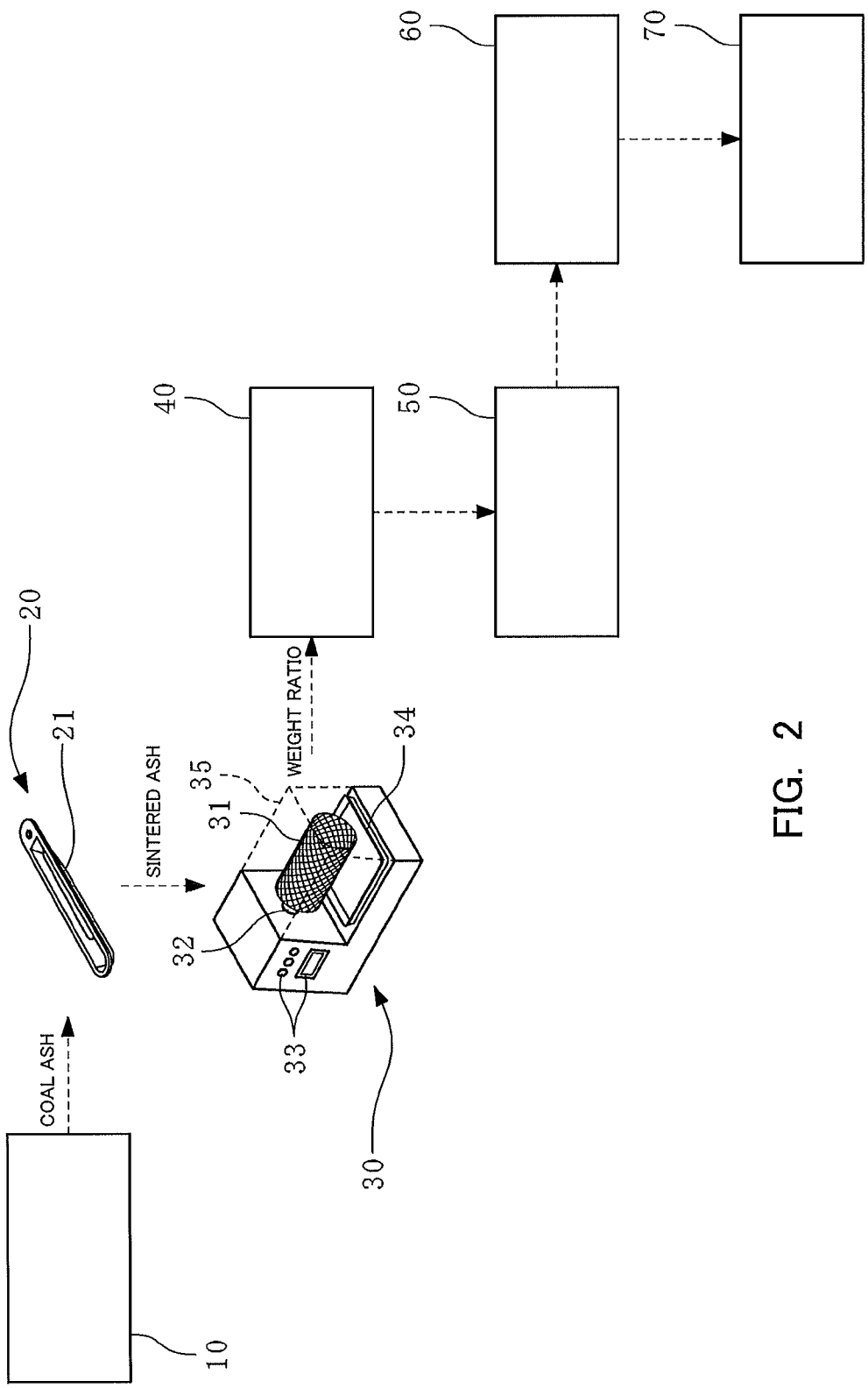
FIG. 2 is an outline block diagram showing an embodiment of an device for predicting ash adhesion in a coal-fired boiler according to the disclosure.

FIGS. 1 and 2 show embodiments of a method and a device for predicting ash adhesion in a coal-fired boiler in the disclosure.

Figure 7:
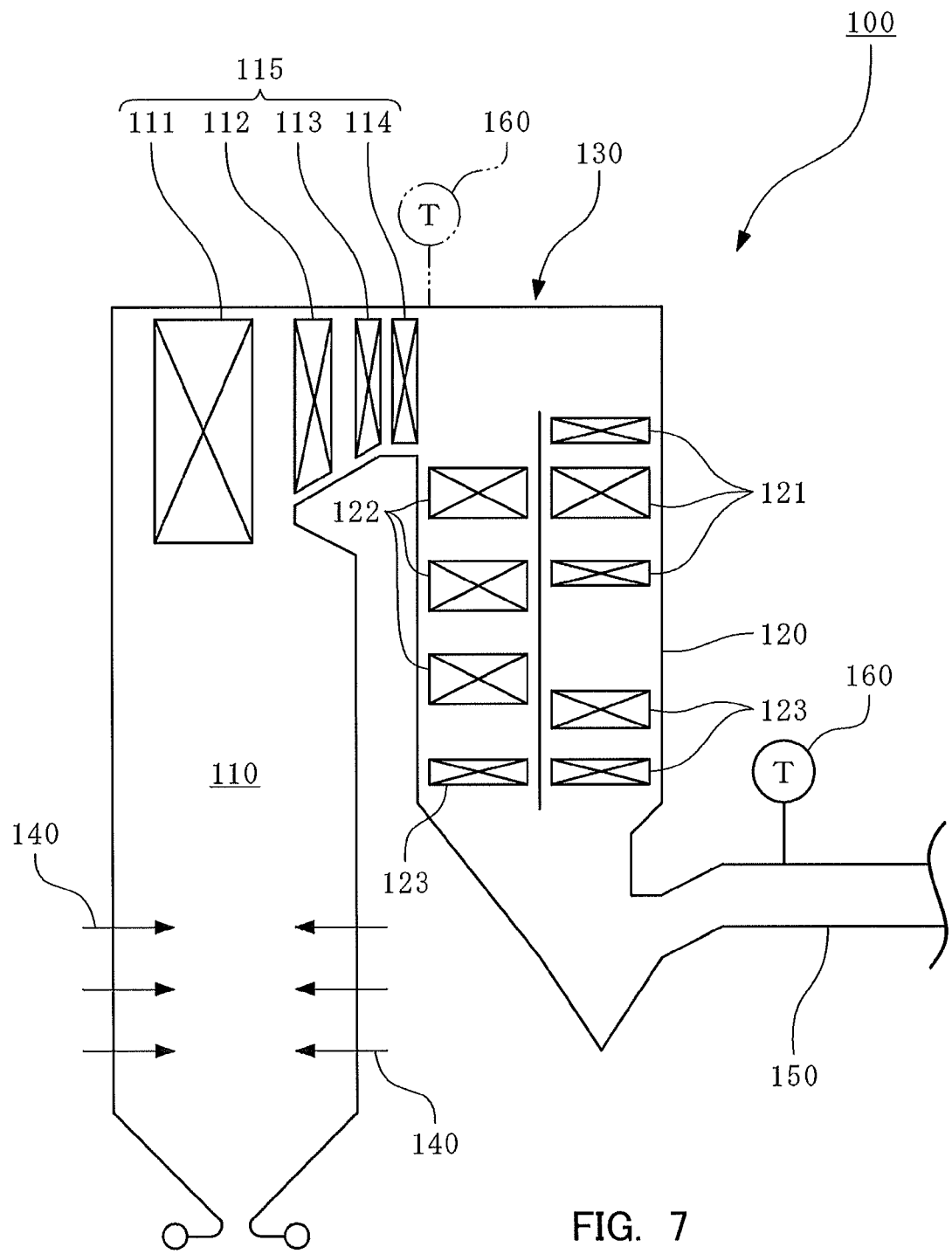
FIG. 7 is a vertical sectional view showing an example of the coal-fired boiler to which the embodiments of the methods and the devices according to the disclosure are applied.

First of all, an example of a coal-fired boiler to which methods and devices according to the disclosure are applied will be schematically described in conjunction with FIG. 7. A coal-fired boiler 100 comprises a boiler body 130 which in turn comprises a furnace 110 provided by furnace wall tubes (heat transmission tubes) and a rear heat transfer unit 120. The boiler body 130 is provided, at a lower portion of the furnace 110, with burners 140 for injecting and burning pulverized coal fuel. The boiler body 130 is provided, at an upper portion of the furnace 110, with secondary, tertiary and final superheaters 111, 112 and 113 and a secondary reheater 114 which provide an upper heat transfer unit 115. The rear heat transfer unit 120 of the boiler body 130 comprises primary superheaters 121, primary reheaters 122 and economizers 123; such heat exchangers are composed of heat transmission tubes. When pulverized coal fuel is injected from the burners 140 for burning into the furnace 100 of the boiler body 130, combustion gas heats the heat transmission tubes constituting the walls of the furnace 110, then heats the upper heat transfer unit 115 at the upper portion of the furnace 110 comprising the secondary, tertiary and final superheaters 111, 112 and 113 and the secondary reheater 114, and then heats the primary superheaters 121, the primary reheaters 122 and the economizers 123 in the rear heat transfer unit 120. The combustion gas (exhaust gas) from which heat has been deprived through heat exchange is guided into a boiler-outlet exhaust gas duct 150; nitrogen oxides, sulfur oxides and the like are removed from the combustion gas by denitration and desulfurization flue-gas treatment devices (not shown) provided downstream; then dust is separated from the combustion gas by a dust collector (not shown) and then the combustion air is discharged to atmosphere.

The embodiment of the method for predicting ash adhesion in the coal-fired boiler comprises, as shown in FIG. 1, a coal-ash generating step, a sintered-ash generating step, a sticking-degree calculating step, a correlation determining step, an exhaust-gas-temperature predicting step and an adhesion predicting step. FIG. 2 is an outline block diagram for a device for predicting ash adhesion in a coal-fired boiler which carries out the method for predicting ash adhesion in the coal-fired boiler.

The coal-ash generating step is a step for asking various kinds of coal such as high- and low-grade coal to be employed as fuel in the coal-fired boiler 100 (see FIG. 7) into coal ash (see step S10 in FIG. 1). Each coal is ashed into coal ash at a temperature of 815° C. in a way conforming to that regulated by JIS. The coal ash is generated by a coal-ash generator 10 shown in FIG. 2.

The sintered-ash generating step is a step for heating the coal ash generated in the coal-ash generating step at a plurality of temperatures within a combustion temperature range of the coal-fired boiler 100 to generate sintered ash at each of the heating temperatures (see step S20 in FIG. 1). The coal ash is sintered such that the coal ash is entered into a magnetic boat 21 as sintered-ash generator 20 as shown in FIG. 2 and is heated at predetermined temperatures. In this case, at a plurality of temperatures (for example, the temperatures with a temperature interval of 50° C.) in a temperature range of about 1000-1400° C. capable of covering at least temperatures around the upper heat transfer unit 115 in the coal-fired boiler 100, heating for sintering is carried out to obtain sintered ash at each of the heating temperatures.

The sticking-degree calculating step is a step for rotatively separating each sintered ash generated in said sintered-ash generating step in a ratra tester 30 (see FIG. 2) to calculate a sticking degree as a weight ratio of the sintered ash after and before the rotary separation thereof (see step S30 in FIG. 1). The ratra tester 30 is used for evaluation of sintered metal and is a device comprising a cylindrical metal mesh 31 (mesh size of 1 mm) with a diameter of the order of 100 mm and with a length of the order of 120 mm and rotated by a rotary shaft 32 at 80 rpm. The ratra tester 30 is such that a sample of the sintered ash is entered into the cylindrical metal mesh 31 rotated at the constant rotation frequency set by a setup section 33, and during the rotation of the metal mesh 31, particles of the sintered ash are separated from the sintered ash and drop through the cylindrical metal mesh 31 onto a passing object pan 34. The cylindrical metal mesh 31 is covered with a cover 35. A weight ratio of the sintered ash after and before the testing is obtained as a sticking degree in a sticking-degree calculator 40 (see FIG. 2). That is, a sticking degree=a weight of sintered ash after the testing/a weight of the sintered ash before the testing.

The correlation determining step is a step for burning each coal having a corresponding sticking degree calculated in the sticking-degree calculating step in the coal-fired boiler 100 to measure an exhaust gas temperature to thereby determine a correlation between sticking degrees and exhaust gas temperatures (see step S40 in FIG. 1). The exhaust gas temperature is measured by a temperature sensor 160 arranged on a boiler outlet exhaust gas duct 150 as shown in FIG. 7. Alternatively, the temperature sensor 160 may be arranged on the outlet portion of the furnace 100 as shown by imaginary lines in FIG. 7 so as to measure the temperature of the exhaust gas having passed through the upper heat transfer unit 115 or the secondary, tertiary and final superheaters 111, 112 and 113 and the secondary reheater 114. The inventors' researches reveal that correlation between sticking degrees and exhaust gas temperatures on coals A-H including, for example, bituminous coal as high-grade coal and subbituminous coal as low-grade coal is as shown by a graph in FIG. 8. The correlation between the sticking degrees and the exhaust gas temperatures is obtained by a correlation determiner 50 (see FIG. 2).

The exhaust-gas-temperature predicting step is a step for predicting an exhaust gas temperature from a sticking degree of coal to be employed as fuel on the basis of the correlation between the sticking degrees and the exhaust gas temperatures obtained in the correlation determining step (see step S50 in FIG. 1). The exhaust gas temperature is predicted from the graph shown in FIG. 8 in an exhaust-gas-temperature predictor 60 (see FIG. 2).

The adhesion predicting step is a step for predicting ash adhesion on the heat transmission tubes in the coal-fired boiler 100 on the basis of the exhaust gas temperature predicted in the exhaust-gas-temperature predicting step (see step S60 in FIG. 1). The ash adhesion on the heat transmission tubes in the coal-fired boiler 100 is predicted in an adhesion predictor 70 (see FIG. 2). The adhesion predictor 70 is adapted to show that the higher the exhaust gas temperature is, the more likely ash may adhere on heat transmission tubes, and may be, for example, of a type in which the predicted ash adhesion on the heat transmission tubes is shown on a screen or attention is drawn by voice.

The sticking-degree calculator 40, the correlation determiner 50, the exhaust-gas-temperature predictor 60 and the adhesion predictor 70 shown in FIG. 2 may be constituted by personal computers.

Next, mode of operation of the embodiments of the above-mentioned method and device for predicting ash adhesion in the coal-fired boiler.

First of all, each of a various kinds of coal such as high- and low-grade coal to be employed as fuel in the coal-fired boiler 100 (see FIG. 7) is ashed in the coal-ash generator 10 shown in FIG. 2 at a temperature of 815° C. in a way conforming to that regulated by JIS (see the coal-ash generating step as step S10 in FIG. 1).

Each coal ash generated in the coal-ash generating step is entered into the magnetic boat 21 as sintered-ash generator as shown in FIG. 2 and is heated at a plurality of temperatures within a combustion temperature range (about 1000° C.-1400° C.) of the coal-fired boiler 100 to thereby generate sintered ash at each of the heating temperatures (see the sintered-ash generating step as step S20 in FIG. 1).

Each sintered ash generated in the sintered-ash generating step is entered into the cylindrical metal mesh 31 in the ratra tester 30 (see FIG. 2) and is rotated at a constant frequency set by the setup section 33, and particles of the sintered ash falling through the cylindrical metal mesh 31 are received by the passing object pan 34. Then, calculated is a ratio of a weight of the sintered ash after the testing to a weight of the sintered ash before the testing:

a sticking degree=a weight of sintered ash after the testing/a weight of the sintered ash before the testing The sticking degree is calculated in the sticking degree calculator 40 (see FIG. 2) (see the sticking-degree calculating step as step S30 in FIG. 1).

Figure 8:
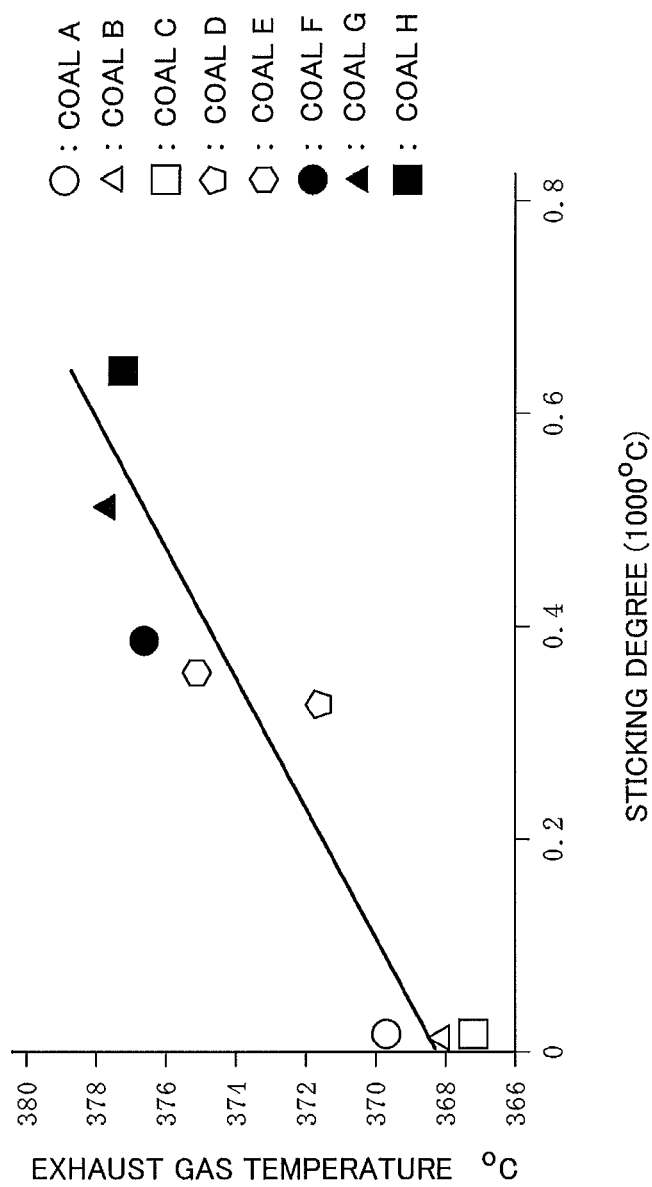
FIG. 8 is a graph showing a correlation between sticking degrees and exhaust gas temperatures in the embodiments of the methods and the devices according to the disclosure.

Each coal with a corresponding sticking degree calculated in the sticking-degree calculating step is burned in the coal-fired boiler 100 to measure an exhaust gas temperature by the temperature sensor 160 (see FIG. 7), so that a correlation between sticking degrees and exhaust gas temperatures is determined as the graph as shown in FIG. 8 in the correlation determiner 50 (see FIG. 2) (see the correlation determining step as step S40 in FIG. 1).

On the basis of the correlation between the sticking degrees and the exhaust gas temperatures obtained in the correlation determining step, an exhaust gas temperature is predicted in the exhaust-gas-temperature predictor 60 (see FIG. 2) from the sticking degree of coal to be employed as fuel (see the exhaust-gas-temperature predicting step as step S50 in FIG. 1). For example, when the sticking degree is 0.4 in the graph shown in FIG. 8, exhaust gas temperature can be predicted to be 374-375° C.

On the basis of the exhaust gas temperature predicted in the exhaust-gas-temperature predicting step, ash adhesion on the heat transmission tubes in the coal-fired boiler 100 is predicted in the adhesion predictor 70 (see FIG. 2) (see the adhesion predicting step as step S60 in FIG. 1). The adhesion predictor 70 indicates the higher the exhaust gas temperature is, the more likely ash may adhere on the heat transmission tubes.

Higher exhaust gas temperature being provided means that ash adheres on the heat transmission tubes to invade heat exchange with the exhaust gas in the heat transmission tubes. That is, when coal providing higher exhaust gas temperature is used as fuel in the coal-fired boiler 100, clogging troubles due to ash adhesion may be caused. The inventors found out that by calculating sticking degrees as coal property parameters to determine the correlation between the sticking degrees and the exhaust gas temperatures in the form of the graph as shown in FIG. 8, an exhaust gas temperature can be predicted on the basis of the sticking degree to predict any ash damages on the basis of the exhaust gas temperature. This is a characteristic feature in the embodiment.

That is to say, if the correlation between the sticking degrees and the exhaust gas temperatures is determined as graph shown in FIG. 8 in the correlation determining step in the embodiment, then merely by calculating a sticking degree of coal to be employed as fuel, an exhaust gas temperature can be predicted to predict any ash adhesion on the heat transmission tubes in the coal-fired boiler 100. In this case, there is no need of shutting down an operation of the coal-fired boiler 100.

In the embodiment, there is no need of actually calculating an actual slag viscosity in an extremely high ambient temperature as high as, for example, 1300° C. as disclosed in Patent Literature 1, which is effective in actually operating the actual coal-fired boiler 100 in safety.

In this manner, the correlation between the sticking degrees and the exhaust gas temperatures can be grasped to suppress lowering of operation availability due to ash damages and economically advantageous low-grade coal can be effectively utilized.

Figure 3:
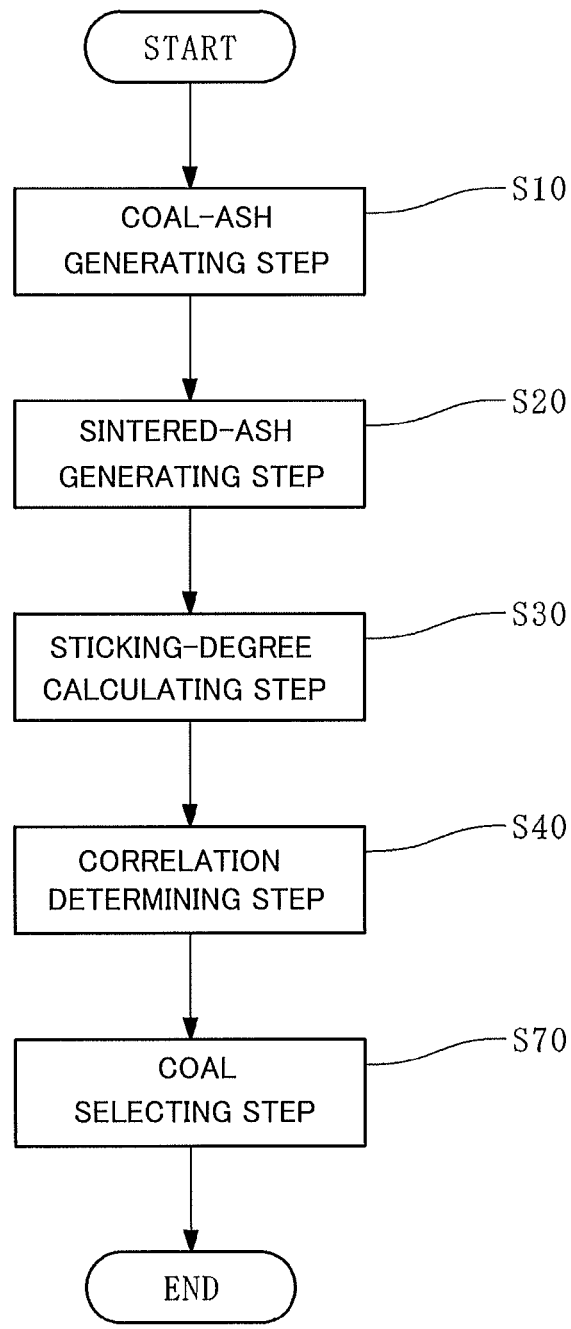
FIG. 3 is a flowchart for showing an embodiment of a method for preventing ash adhesion in a coal-fired boiler according to the disclosure.
Figure 4:
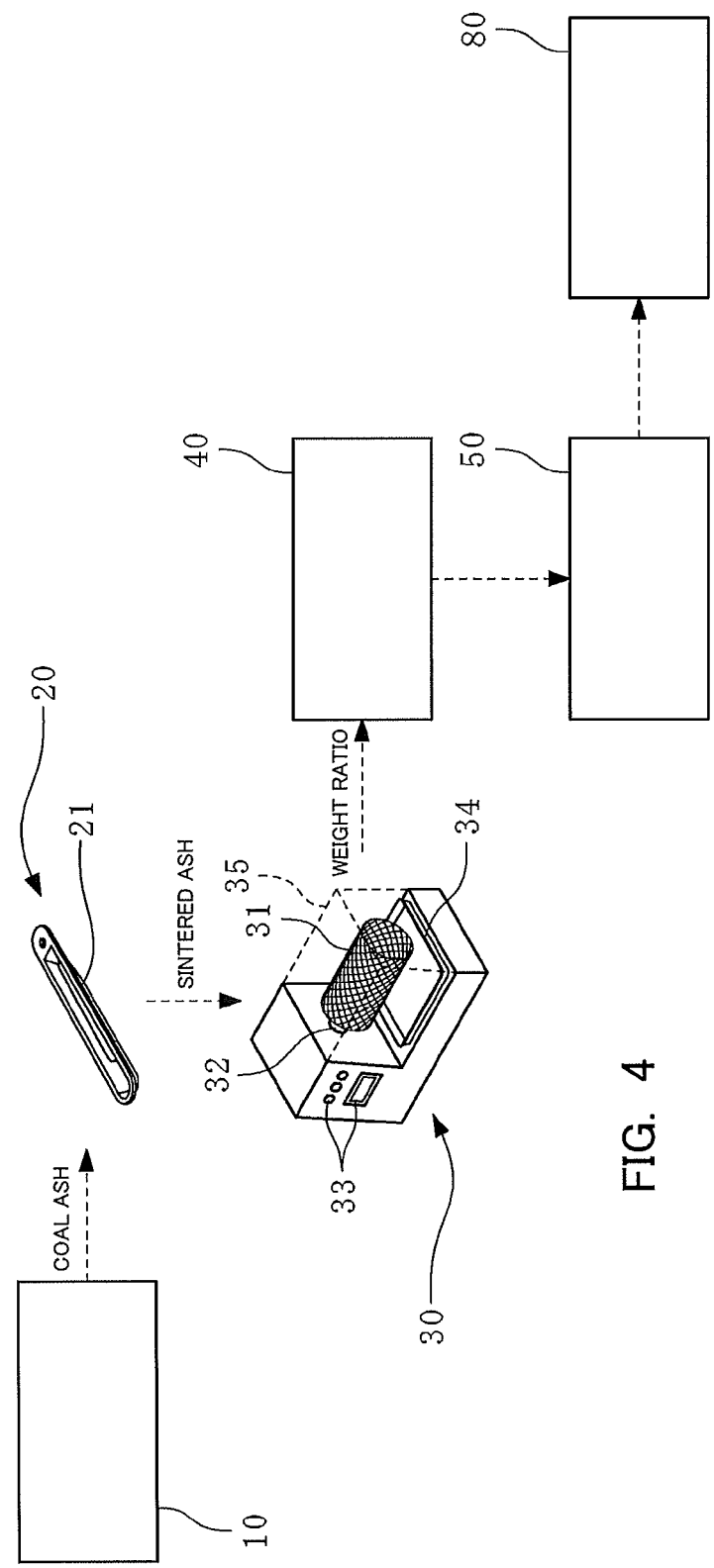
FIG. 4 is an outline block diagram showing an embodiment of a device for preventing ash adhesion in a coal-fired boiler according to the disclosure.

FIGS. 3 and 4 show embodiments of a method and a device for preventing ash adhesion in a coal-fired boiler in the disclosure. In these Figures, parts similar to those in FIGS. 1 and 2 are represented by the same reference numerals; fundamental structure thereof is similar to that in the method and the device for predicting ash adhesion in the coal-fired boiler shown in FIGS. 1 and 2.

The method for preventing ash adhesion in the coal-fired boiler according to the embodiment comprises, as shown in FIG. 3, a coal-ash generating step, a sintered-ash generating step, an sticking-degree calculating step, a correlation determining step and a coal selecting step. FIG. 4 shows an outline of the device for preventing ash adhesion in the coal-fired boiler which can carry out the method for preventing ash adhesion in the coal-fired boiler.

Explanation on the coal-ash generating step, the sintered-ash generating step, the sticking-degree calculating step and the correlation determining step in the method for preventing ash adhesion in the coal-fired boiler shown in FIG. 3 are omitted since they are similar to those in the method for predicting ash adhesion in the coal-fired boiler shown in FIG. 1. Moreover, explanation on the coal-ash generator 10, the sintered-ash generator 20, the ratra tester 30, the sticking degree calculator 40 and the correlation determiner 50 in the device for preventing ash adhesion in the coal-fired boiler shown in FIG. 4 are omitted since they are similar to those in the device for predicting ash adhesion in the coal-fired boiler shown in FIG. 2.

The coal selecting step is a step for selecting the coal having a sticking degree as fuel so as to provide an exhaust gas temperature not higher than a set value on the basis of the correlation between the sticking degrees and the exhaust gas temperatures obtained in the correlation determining step (see step S70 in FIG. 3). Coal is selected by a coal selector 80 (see FIG. 4). Stored in the coal selector 80 are data on sticking degrees on single kinds of coal and on a plural kinds of coal mixed, so that usable coal (single one or mixed one) may be selected on the basis of the data on the sticking degrees and the correlation data. The set value for the exhaust gas temperature may be set, for example, of the order of 374-376° C. However, this does not mean that restriction is made to these temperatures.

The sticking degree calculator 40, the correlation determiner 50 and the coal selector 80 shown in FIG. 4 may be constituted by personal computers.

Next, mode of operation of the above-mentioned method and device for preventing ash adhesion in the coal-fired boiler will be described.

In the method and the device for preventing ash adhesion in the coal-fired boiler shown in FIGS. 3 and 4, steps from the coal-ash generating step to the correlation determining step are conducted similarly to those in the method and the device for predicting ash adhesion in the coal-fired boiler shown in FIGS. 1 and 2.

Then, on the basis of the correlation between the sticking degrees and the exhaust gas temperatures obtained in the correlation determining step, coal with a sticking degree to be used as fuel is selected by the coal selector 80 (see FIG. 4) so as to provide an exhaust gas temperature not higher than a set value (for example, of the order of 374-376° C.)(see the coal selecting step as step S70 in FIG. 3).

When coal selected by the coal selector 80 is used as fuel, the exhaust gas temperature can be suppressed to be not higher than the set value so that ash hardly adheres on the heat transmission tubes and heat exchange with the exhaust gas on the heat transmission tubes is hardly blocked.

Thus, the operation of the actual coal-fired boiler 100 can be stably continued. Incidentally, if forced shutdown due to ash damages can be averted once in an electric generation plant having a generation capacity of the order of 600 MW, loss of 100 million yen or more can be suppressed.

Thus, also in the method and the device for preventing ash adhesion in the coal-fired boiler shown in FIGS. 3 and 4, just like the method and the device for predicting ash adhesion in the coal-fired boiler shown in FIGS. 1 and 2, the correlation between the sticking degrees and the exhaust gas temperatures can be grasped to suppress lowering of operation availability due to ash damages, and economically advantageous low-grade coal can be effectively utilized.

Figure 5:
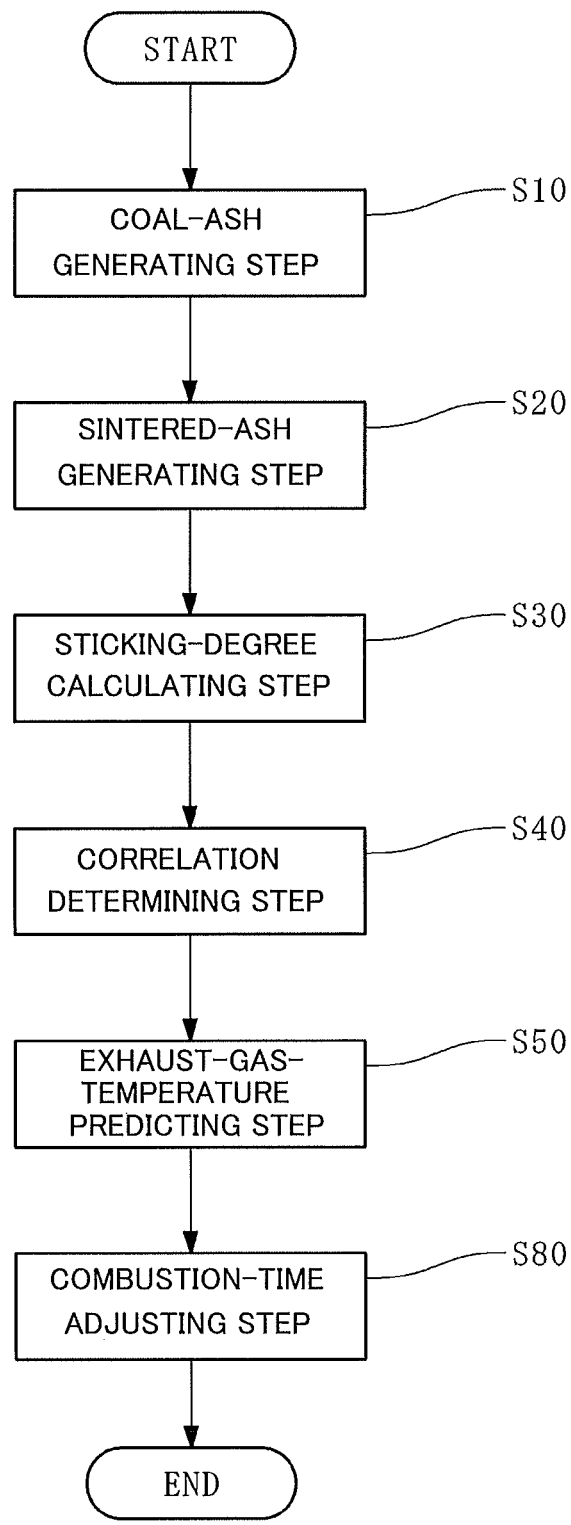
FIG. 5 is a flowchart showing an embodiment of a method for operating a coal-fired boiler according to the disclosure.
Figure 6:
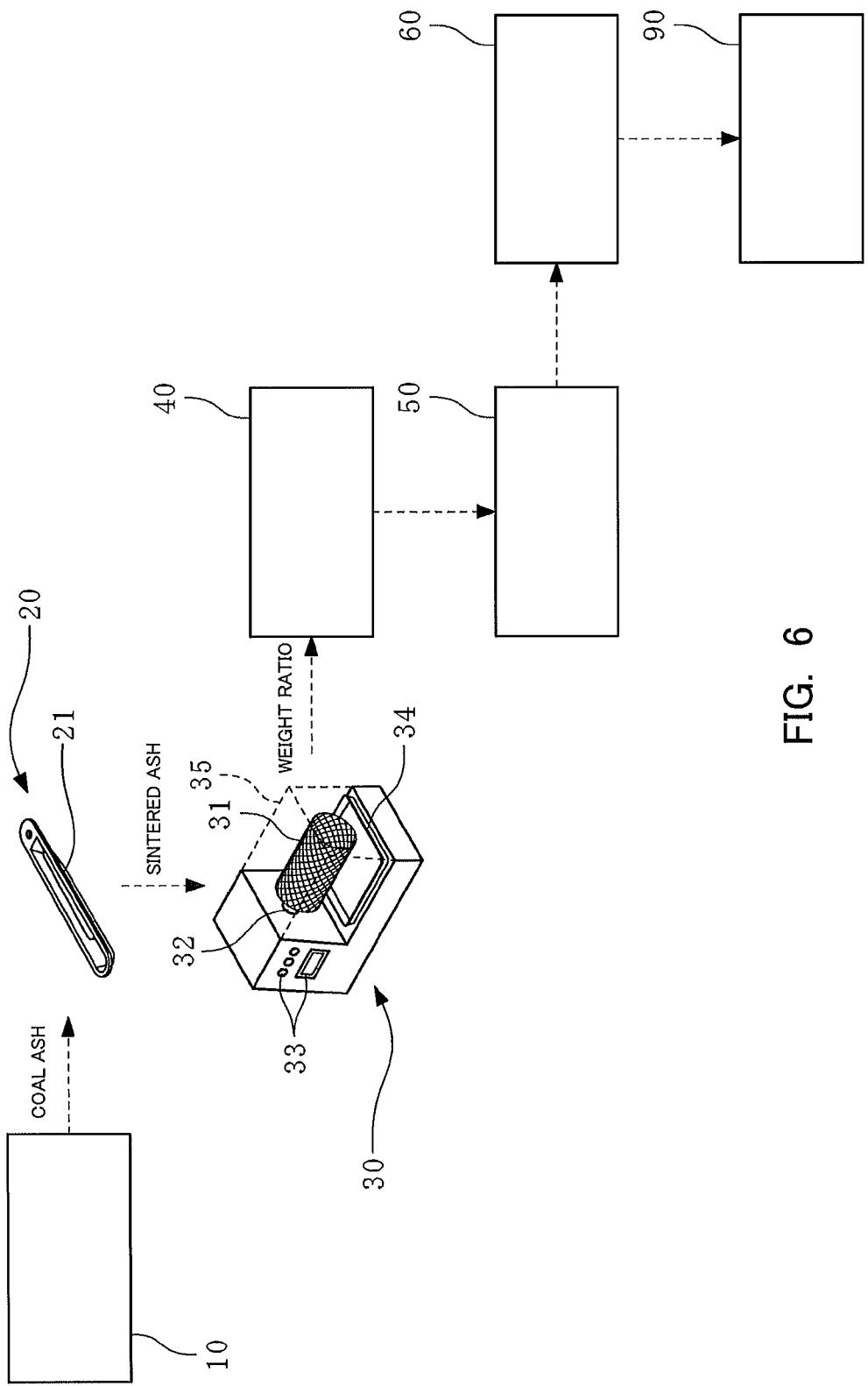
FIG. 6 is an outline block diagram showing an embodiment for a device for operating a coal-fired boiler according to the disclosure.

FIGS. 5 and 6 show an embodiment for operating a coal-fired boiler in the disclosure. In these figures, parts similar to those in FIGS. 1 and 2 and FIGS. 3 and 4 are represented by the same reference numerals; fundamental structure thereof is similar to those shown in the method and the device for predicting ash adhesion in the coal-fired boiler shown in FIGS. 1 and 2 and those shown in the method and the device for preventing ash adhesion in the coal-fired boiler shown in FIGS. 3 and 4.

The method for operating the coal-fired boiler in the embodiment comprises, as shown in FIG. 5, a coal-ash generating step, a sintered-ash generating step, a sticking-degree calculating step, a correlation determining step, an exhaust-gas-temperature predicting step and a combustion-time adjusting step. FIG. 6 shows an outline of the device for operating the coal-fired boiler which carries out the method for operating the coal-fired boiler.

Explanation on the coal-ash generating step, the sintered-ash generating step, the sticking-degree calculating step, the correlation determining step and the exhaust-gas-temperature predicting step in the method for operating the coal-fired boiler shown in FIG. 5 are omitted since they are similar to those in the method for predicting ash adhesion in the coal-fired boiler shown in FIG. 1. Moreover, explanation on the coal-ash generator 10, the sintered-ash generator 20, the ratra tester 30, the sticking-degree calculator 40, the correlation determiner 50 and the exhaust-gas-temperature predictor 60 in the device for operating the coal-fired boiler shown in FIG. 6 is omitted since they are similar to those in the device for predicting ash adhesion in the coal-fired boiler shown in FIG. 2.

The combustion-time adjusting step is a step for adjusting a combustion time of coal on the basis of an exhaust gas temperature predicted in the exhaust-gas-temperature predicting step (see step S80 in FIG. 5). The combustion time of the coal is adjusted by a combustion-time adjuster 90 (see FIG. 6). The combustion-time adjuster 90 has a function of, for example, outputting a control signal to the burners 140 (see FIG. 7) to restrict a time for injecting the pulverized coal fuel from the burners 140 into the furnace 110.

The sticking degree calculator 40, the correlation determiner 50, the exhaust-gas-temperature predictor 60 and the combustion-time adjuster 90 shown in FIG. 6 may be constituted by personal computers.

Next, mode of operation of the embodiments of the method and device for operating the coal-fired boiler will be described.

In the method and device for operating the coal-fired boiler shown in FIGS. 5 and 6, steps from the coal-ash generating step to the exhaust-gas-temperature predicting step are conducted similarly to those in the method and the device for predicting ash adhesion in the coal-fired boiler shown in FIGS. 1 and 2.

Then, the combustion time of the coal is adjusted by combustion-time adjuster 90 (see FIG. 6) on the basis of an exhaust gas temperature predicted in the exhaust-gas-temperature predicting step (see the combustion-time adjusting step as step S80 in FIG. 5).

For example, use of coal G or coal H or a mixture thereof in the graph shown in FIG. 8 provides sticking degree of 0.5 or more, assumingly resulting in exhaust gas temperature over 376° C. However, even in such a case, ash adhesion on the heat transmission tubes may be suppressed by setting the combustion time shorter; then, coal may be changed over into one with a sticking degree capable of suppressing the exhaust gas temperature to a lower value.

Thus, ash adhesion on the heat transmission tubes can be suppressed to effectively utilize low-grade coal, thereby stably continuing the operation of the actual coal-fired boiler 100 with higher economic advantages. Incidentally, if fuel cost can be reduced by 1% in an electric generation plant with a capacity of the order of 600 MW, total cost can be reduced by about 200 million yen per year.

Thus, also in the method and the device for operating the coal-fired boiler shown in FIGS. 5 and 6, just like the method and the device for predicting ash adhesion in the coal-fired boiler shown in FIGS. 1 and 2 and the method and the device for preventing ash adhesion in the coal-fired boiler shown in FIGS. 3 and 4, the correlation between the sticking degrees and the exhaust gas temperatures can be grasped to suppress lowering of operation availability due to ash damages and economically advantageous low-grade coal can be effectively utilized.

In each of the method and the device for predicting ash adhesion in the coal-fired boiler shown in FIGS. 1 and 2, the method and the device for preventing ash adhesion in the coal-fired boiler shown in FIGS. 3 and 4 and the method and the device for operating the coal-fired boiler shown in FIGS. 5 and 6, a single kind of coal may be, of course, used as fuel; alternatively, the coal may be a plurality kinds of coal mixed. In the latter case, a mixture comprising high-grade coal in the form of bituminous coal and low-grade coal in the form of, for example, subbituminous coal, high-silica coal, high-sulfur coal, high-calcium coal or high-ash coal as need demands becomes more effective in enhancing economic advantages on fuel cost.

It is to be understood that a method and an device for predicting ash adhesion in a coal-fired boiler, a method and an device for preventing ash adhesion in a coal-fired boiler and a method and an device for operating a coal-fired boiler according to the disclosure are not limited to the above embodiments and that various changes and modifications may be made without departing from the scope of the disclosure.

REFERENCE SIGNS LIST 10 coal-ash generator
20 sintered-ash generator
21 magnetic boat
30 ratra tester
31 cylindrical metal mesh
32 rotary shaft
33 setup section
34 passing object pan
35 cover
40 sticking-degree calculator
50 correlation determiner
60 exhaust-gas-temperature predictor
70 adhesion predictor
80 coal selector
90 combustion-time adjuster
100 coal-fired boiler
110 furnace
111 secondary superheater
112 tertiary superheater
113 final superheater
114 secondary reheater
115 upper heat transfer unit
120 rear heat transfer unit
121 primary superheater
122 primary reheater
123 coal economizer
130 boiler body
140 burner
150 boiler outlet exhaust gas duct
160 temperature sensor

The invention claimed is:

1. A method for predicting ash adhesion in a coal-fired boiler comprising
   a coal-ash generating step for aching coal into coal ash,
   a sintered-ash generating step for heating the coal ash generated in said coal-ash generating step at a plurality of temperatures within a combustion temperature range of the coal-fired boiler to generate sintered ash at each of the heating temperatures,
   a sticking-degree calculating step for rotatively separating each sintered ash generated in said sintered-ash generating step by a ratra tester to calculate a sticking degree from a weight ratio of the sintered ash after and before the rotary separation thereof,
   a correlation determining step for burning each coal having a corresponding sticking degree calculated in said sticking-degree calculating step in the coal-fired boiler to measure exhaust gas temperatures to thereby determine correlation between sticking degrees and exhaust gas temperatures,
   an exhaust-gas-temperature predicting step for predicting an exhaust gas temperature from a sticking degree of coal to be employed as fuel on the basis of the correlation between the sticking degrees and the exhaust gas temperatures obtained in said correlation determining step and, an adhesion predicting step for predicting ash adhesion in the coal-fired boiler on the basis of the exhaust gas temperature predicted in said exhaust-gas-temperature predicting step.

2. The method for predicting ash adhesion in the coal-fired boiler as claimed in claim 1, wherein said coal is a mixture of a plurality kinds of coal.

3. An device for predicting ash adhesion in a coal-fired boiler comprising a coal-ash generator for ashing coal into coal ash, a sintered-ash generator for heating the coal ash generated in said coal-ash generator at a plurality of temperatures within a combustion temperature range in the coal-fired boiler to generate sintered ash at each of the heating temperatures, a ratra tester for rotatively separating each sintered ash generated in said sintered-ash generator, a sticking-degree calculator for calculating a sticking degree from a weight ratio of each sintered ash after and before the rotary separation thereof by said ratra tester, a correlation determiner for burning each coal having a corresponding sticking degree calculated in said sticking-degree calculator in the coal-fired boiler to measure the exhaust gas temperature to thereby determine a correlation between sticking degrees and exhaust gas temperatures, an exhaust-gas-temperature predictor for predicting an exhaust gas temperature from a sticking degree of coal to be employed as fuel on the basis of the correlation between the sticking degrees and the exhaust gas temperatures obtained in said correlation determiner and an adhesion predictor for predicting ash adhesion in the coal-fired boiler on the basis of the exhaust gas temperature predicted in said exhaust-gas-temperature predictor.

4. The device for predicting ash adhesion in the coal-fired boiler as claimed in claim 3, wherein said coal is a mixture of a plurality of kinds of coal.

5. A method for preventing ash adhesion in a coal-fired boiler comprising a coal-ash generating step for ashing coal into coal ash, a sintered-ash generating step for heating the coal ash generated in said coal-ash generating step at a plurality of temperatures within a combustion temperature range of the coal-fired boiler to generate sintered ash at each of the heating temperatures, a sticking-degree calculating step for rotatively separating each sintered ash generated in said sintered-ash generating step by a ratra tester to calculate a sticking degree from a weight ratio of the sintered ash after and before the rotary separation thereof, a correlation determining step for burning each coal having a corresponding sticking degree calculated in said sticking-degree calculating step in the coal-fired boiler to measure an exhaust gas temperature to thereby determine a correlation between sticking degrees and exhaust gas temperatures and a coal selecting step for selecting coal having a sticking degree as fuel so as to provide an exhaust gas temperature not higher than a set value on the basis of the correlation between the sticking degrees and the exhaust gas temperatures obtained in said correlation determining step.

6. The method for preventing ash adhesion in the coal-fired boiler as claimed in claim 5, wherein said coal is a mixture of a plurality kinds of coal.

7. A device for preventing ash adhesion in a coal-fired boiler comprising a coal-ash generator for ashing coal into coal ash, a sintered-ash generator for heating the coal ash generated in said coal-ash generator at a plurality of temperatures within a combustion temperature range of the coal-fired boiler to generate sintered ash at each of the heating temperatures, a ratra tester for rotatively separating each sintered ash generated in said sintered-ash generator, a sticking-degree calculator for calculating a sticking degree from weight ratio of each sintered ash after and before the rotary separation thereof by said ratra tester, a correlation determiner for burning each coal having a corresponding sticking degree calculated in said sticking-degree calculator in the coal-fired boiler to measure an exhaust gas temperature to thereby determine a correlation between sticking degrees and exhaust gas temperatures and a coal selector for selecting coal as fuel with a sticking degree as fuel so as to provide an exhaust gas temperature not higher than a set value on the basis of the correlation between the sticking degrees and the exhaust gas temperatures obtained in said correlation determiner.

8. The device for preventing ash adhesion in the coal-fired boiler as claimed in claim 7, wherein said coal is a mixture of a plurality of kinds of coal.

9. A method for operating a coal-fired boiler comprising a coal-ash generating step for ashing coal into coal ash, a sintered-ash generating step for heating the coal ash generated in said coal-ash generating step at a plurality of temperatures within a combustion temperature range of the coal-fired boiler to generate sintered ash at each of the heating temperatures, a sticking-degree calculating step for rotatively separating each sintered ash generated in said sintered-ash generating step by a ratra tester to calculate a sticking degree from a weight ration of the sintered ash after and before the rotary separation thereof, a correlation determining step for burning each coal having a corresponding sticking degree calculated in said sticking-degree calculating step in the coal-fired boiler to measure an exhaust gas temperature to thereby determine a correlation between sticking degrees and exhaust gas temperatures, an exhaust-gas-temperature predicting step for predicting an exhaust gas temperature from a sticking degree of coal to be employed as fuel on the basis of the correlation between the sticking degrees and the exhaust gas temperatures obtained in said correlation determining step and a combustion-time adjusting step for adjusting a combustion time of said coal on the basis of the exhaust gas temperature predicted in said exhaust-gas-temperature predicting step.

10. The method for operating the coal-fired boiler as claimed in claim 9, wherein said coal is a mixture of a plurality kinds of coal.

11. A device for operating a coal-fired boiler comprising
a coal-ash generator for ashing coal into coal ash,
a sintered-ash generator for heating the coal ash generated in said coal-ash generator at a plurality of temperatures within a combustion temperature range of the coal-fired boiler to generate sintered ash at each of the heating temperatures,
a ratra tester for rotatively separating each sintered coal generated in said sintered-ash generator,
a sticking-degree calculator for calculating sticking degree from weight ratio of each sintered ash after and before the rotary separation thereof by said ratra tester,
a correlation determiner for burning each coal having a corresponding sticking degree calculated in said sticking degree calculator in the coal-fired boiler to measure an exhaust gas temperature to thereby determine a correlation between sticking degrees and exhaust gas temperatures,
an exhaust-gas-temperature predictor for predicting an exhaust gas temperature from a sticking degree of coal to be employed as fuel on the basis of the correlation between the sticking degrees and the exhaust gas temperatures obtained in said correlation determiner and
a combustion-time adjuster for adjusting a combustion time of said coal on the basis of the exhaust gas temperature predicted in said exhaust-gas-temperature predictor.

12. The device for operating the coal-fired boiler as claimed in claim 11, wherein said coal is a mixture of a plurality of kinds of coal.

\* \* \* \* \*